United States Patent [19]

Nguyen et al.

[11] Patent Number: 5,138,647
[45] Date of Patent: Aug. 11, 1992

[54] PORTAL IMAGING DEVICE

[75] Inventors: John Nguyen, Pleasant Hill; Cedric X. Yu, Martinez, both of Calif.

[73] Assignee: Siemens Medical Laboratories, Inc., Concord, Calif.

[21] Appl. No.: 562,184

[22] Filed: Aug. 3, 1990

[51] Int. Cl.$^5$ .............................................. H01J 31/49
[52] U.S. Cl. .................................... 378/189; 378/190; 378/193; 378/62
[58] Field of Search .................... 378/189, 62, 190, 19, 378/193, 22, 65

[56] References Cited

U.S. PATENT DOCUMENTS

| | | | |
|---|---|---|---|
| 2,505,853 | 6/1940 | Jany | 250/65 |
| 4,890,313 | 12/1989 | Lam et al. | 378/189 |
| 4,995,068 | 2/1991 | Chou et al. | 378/189 |

FOREIGN PATENT DOCUMENTS 0259989  3/1988  European Pat. Off. .
2076786  10/1971  France .
2165730  4/1986  United Kingdom .

OTHER PUBLICATIONS

"A Primer on Theory and Operation of Linear Accelerators in Radiation Therapy", U.S. Dept. of Commerce, National Technical Information Service, Dec. 1981.
"Use of Digital Fluoroscopy as an On-Line Verification Device in Radiation Therapy", J. Leong in Phys. Med. Biol., 1986, vol. 31, No. 9, pp. 985–992.
"Therapy Imaging: A signal-to-noise analysis of metal plate/film detectors", Munro et al. in Med. Phys. 14 (6), Nov./Dec. 1987, pp. 975–984.
"Fluoroscopic Visualization of Megavoltage Therapeutic X Ray Beams", Baily et al. in Int. J. Radiation Oncology Biol. Phys., vol. 6, 1980, pp. 935–939.
"Video Techniques for On-line Portal Imaging" by Shalev et al., in Computerized Medical Imaging and Graphics, vol. 13, No. 3, 1989, pp. 217–226.
International Search Report PCT/US 91/05523.

Primary Examiner—Janice A. Howell
Assistant Examiner—Don Wong
Attorney, Agent, or Firm—Lawrence C. Edelman

[57] ABSTRACT

A radiation treatment apparatus is provided which has an extendable imaging device. The radiation treatment apparatus comprises a stand which supports a gantry in a rotable manner. The gantry has a treatment head for emitting a radiation beam towards an object. The extendable imaging device is coupled to the gantry opposite to the treatment head in the trajectory of the radiation beam at a point past the object. The imaging device includes an holding means which is extendable from the gantry one end of which is arranged at the gantry and at the other end of which a detector head is coupled. The detector head comprises an image converting means which in its operating position is essentially perpendicular to the radiation beam and which converts an image represented by the radiation beam into a visible image. It also comprises a reflector coupled with the image converting means for reflecting the visible image into a light channel formed by the holding means and to a video camera. In a preferred embodiment of the invention the image converting means is collapsible and the reflector is formed as a mirror and is foldable towards the image converting means.

26 Claims, 4 Drawing Sheets

PORTAL IMAGING DEVICE

BACKGROUND OF THE INVENTION

1. Field of the Invention

This invention relates generally to portal imaging devices for radiation treatment systems, and more particularly to imaging devices for linear accelerators (linacs) used in radiation therapy.

2. Description of the Prior Art

The use of a linear accelerators in radiation therapy is generally known and is described e.g. in the brochure "A primer on Theory and Operation of Linear Accelerators in Radiation Therapy", U.S. Department of Commerce, National Technical Information Service December 1981. Such linear accelerators are used for treating patients with X-rays or electron beams. Such X-rays are created when high energy electrons are decelerated in a target material such as tungsten. Alternatively, the electrons themselves may be used directly for treatment.

The major modules in a linear accelerator are a gantry with treatment head, a stand, a control console and a treatment couch. The stand is anchored firmly to the floor and the gantry rotates on bearings in the stand. The operational accelerator structure, housed in the gantry, rotates about a horizontal axis fixed by the stand for treatment of a patient laying on the treatment couch.

In the radiation therapy treatment of a patient, geometric accuracy is a very important factor to the success of the treatment. From the article "Use of Digital Fluoroscopy as an On-line Verification Device in Radiation Therapy" by Joseph Leong in Phys. Med. Biol., 1986, Vol. 31, No. 9, 985-992, several methods for local control of the delivery of radiation are known. These methods are portal verification films and record-and-verify systems.

Portal verification films do not deliver images of sufficient quality in certain situations, particularly when high energy X-rays are used in the treatment and they need a relatively long time to develop. Furthermore, films are expensive and the images can only be seen after the treatment dose has been delivered.

A known record-and-verify system includes an imaging section for delivering an image using a fluoroscopic technique and an image processing section for digitally processing the image. In the imaging section a fluorescent screen converts images generated by the X-rays, which are emitted from the treatment head and then pass through the patient, into visible images. The visible images are then reflected to a video camera by a reflector in order to avoid irradiating the camera. In the image processing section the video signals from the camera are digitally processed in real-time for continuous monitoring of the treatment field throughout the treatment.

Known portal imaging devices have been enclosed in rigid light tight boxes. In order for the boxes to cover a reasonable radiation field size, the construction of the detector enclosure has to be very bulky, which poses an inconvenience during patient set-up and occupies space in the treatment room when not being used. Practical use of such devices is thus limited.

SUMMARY OF THE INVENTION

1. Objects

It is an object of the present invention to provide a radiation treatment apparatus having a portal imaging device which offers great convenience and which does not require extra space for storage.

2. Summary

In accordance with the present invention there is provided a radiation treatment apparatus having an extendable imaging device. The radiation treatment apparatus comprises a stand which supports a gantry in a rotatable manner. The gantry has a treatment head at one end thereof for emitting a radiation beam towards an object. The extendable imaging device is coupled to another end of the gantry, which is opposite to the treatment head in the trajectory of the radiation beam and at a point past the object. The imaging device includes an extendable holding means, one end of which is arranged at the gantry and at the other end of which is coupled to a detector head. The detector head comprises an image converting means which in its operating position is essentially perpendicular to the radiation beam and which converts an image represented by the radiation beam into a visible image. The detector head also comprises a reflector coupled with the image converting means for reflecting the visible image through a light channel formed by the holding means to a video camera.

In a preferred embodiment of the invention the image converting means is collapsible and the reflector is formed as a mirror which is foldable with the image converting means.

A high percentage of linear accelerators do not include a beam stopper mechanism at the gantry opposite to the treatment head, and therefore space reserved inside the gantry for the beam stopper mechanism can instead be used to mount and store the extendable imaging device.

Additional features and objects of the invention will be more readily appreciated and better understood by reference to the following detailed description which should be considered in conjunction with the drawings.

DESCRIPTION OF THE PREFERRED EMBODIMENT OF THE INVENTION

Figure 1:
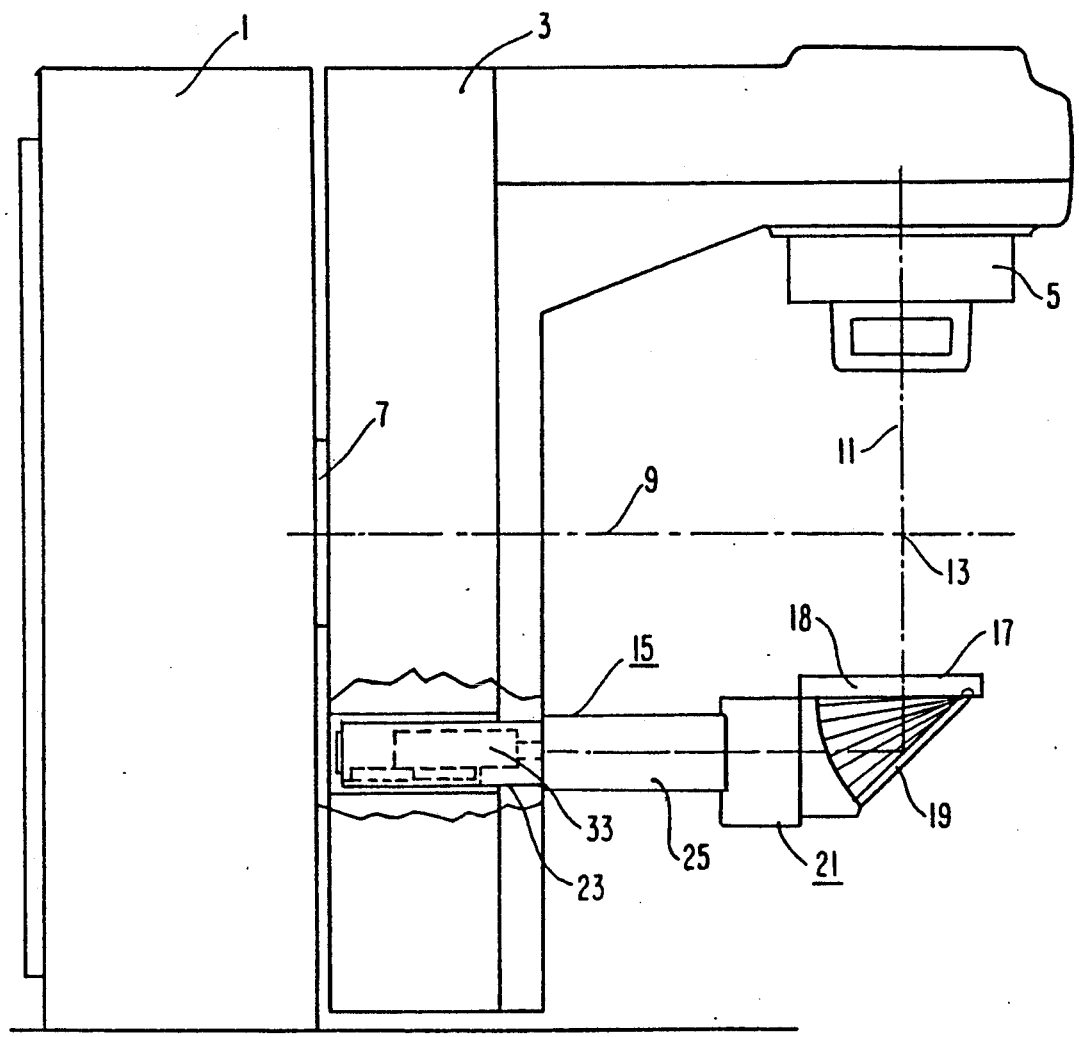
FIG. 1 depicts a radiation beam treatment apparatus having a retractable and collapsible imaging device which is shown in its extended and unfolded "ready for use" position.

In FIG. 1 of the drawings there is shown a radiation therapy apparatus comprising a stand 1 anchored firmly to the floor. Stand 1 supports a gantry 3 including a treatment head 5. Gantry 3 can be rotated on bearings 7 around a horizontal axis 9. Treatment head 5 emits a treatment beam 11 which might be an X-ray beam or an electron beam. The X-rays usually are of penetrating power and are used for the treatment of deep seated tumors, whereas the electrons themselves may be used directly to treat more superficial cancers. The patient rests on a treatment couch (not shown) and meets the treatment area at an isocenter 13.

In stand 1 an electron injector is provided which supplies injector pulses to an electron gun arranged in gantry 3. Electrons are emitted from the electron gun into an evacuated waveguide for acceleration. An electromagnetic field supplied to the waveguide accelerates the electrons emitted by the electron gun for forming an electron beam. In treatment head 5 the electron beam enters an evacuated envelope which bends the electron beam by 270 degrees. The electron beam then leaves the envelope through a window (not shown). If electron radiation is to be generated, a scattering foil is moved into the trajectory of the electron beam and if X-ray radiation is to be generated, a target is moved into the trajectory. The energy level of the electron beam is caused to be higher than during the generation of the electron radiation because more energy is necessary for generating X-ray radiation due to deceleration of the electrons in the target. The construction and operation of the radiation therapy device as described so far is conventional and explained, e.g. in the brochure "A primer on Theory and Operation of Linear Accelerators in Radiation Therapy", U.S. Department of Commerce, National Technical Information Service, December 1981.

At the front surface of the side of gantry 3 which is opposite to treatment head 5 there is arranged a retractable and collapsible imaging device 15 which allows radiation treatment simultaneously with visualization of the patient's anatomy within the X-ray radiation beam. Since the X-ray radiation beam has high photon energy, a normal X-ray fluoroscopic system does not deliver an X-ray image having sufficient contrast. Therefore, imaging device 15 comprises in an image converter 17 which is a part of a detector head 21, a heavy metal foil and a thin fluorescent foil (both foils not shown). After passing through the patient's body, the X-rays impinge first on the metal foil and create electrons. In the fluorescent foil, the X-rays and the electrons emitted from the metal foil stimulate the generation of visible light. By the use of the metal foil, the light output of the fluorescent foil is increased so that the generated X-ray images provide sufficient contrast. The visible light emitted from the fluorescent foil is transmitted via a reflector 19, preferably a mirror angled at 45 degrees, to a visible light sensitive video camera 33 positioned inside gantry 3 and therefore behind it's front surface. The foils are held in a screen frame 18 which is part of image converter 17. The whole imaging device 15 is encased in a light-tight housing which comprises an extendable, preferably telescopic, holding portion and the detector head 21, including image converter 17 and reflector 19. The extendable holding portion comprises two tubes 23 and 25 which are connected by linear bearings mounted therebetween, to ensure minimal deflection in all directions and easy operation. In the telescopic portion, larger diameter tube 25 is shifted over small diameter tube 23 so that a larger field of view for video camera 33 can be provided. When extended, the holding telescopic portion and detector head 21 are preferably automatically locked to form a rigid and light-tight enclosure which forms a light channel between reflector 19 and video camera 33.

Since imaging device 15 is mounted on gantry 3, portal images can be obtained at any gantry angle and during rotation of gantry 3.

Figure 2:
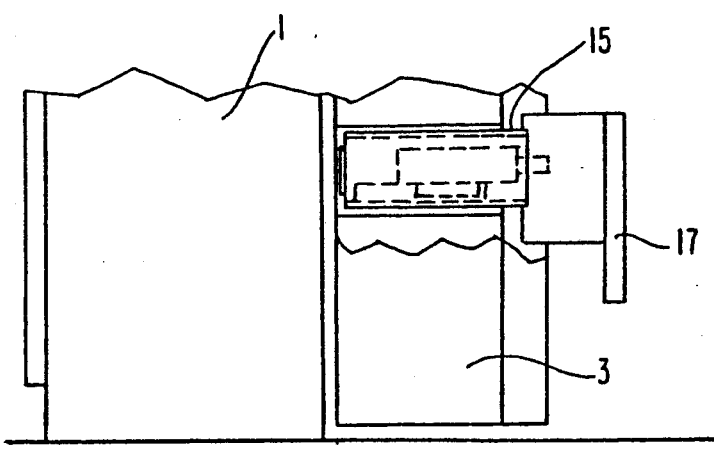
FIG. 2 shows the imaging device in its retracted and collapsed "storage" position.

FIG. 2 shows the radiation therapy apparatus with imaging device 15 in its retracted and collapsed position. In detector head 21, image converter 17 and reflector 19 are in their folded position. Thus, imaging system 15 does not require additional storage space and does not pose any inconveniences when not in use during patient set-up.

In FIGS. 3 to 6 imaging device 15 is shown in various stages from the retracted and collapsed storage position to the extended and unfolded use position.

Figure 3:
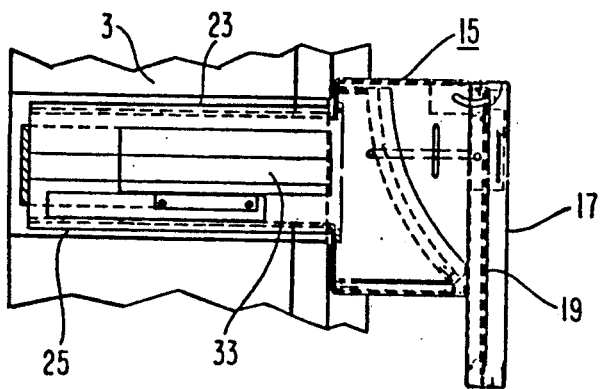
FIGS. 3, 4, 5 and 6 depict the imaging device at various stages from the retracted and collapsed position to its extended and unfolded working position.

FIG. 3 shows imaging device 15 in its retracted and collapsed storage position. Tube 23 is fastened to a rear wall of gantry 3 through the rear opening of the tube 23. Inside tube 23 video camera 33 is arranged. Linear slides with ball bearings 35 are fastened to the top, bottom and each side wall of tube 23 for carrying tube 25 therein in a sliding manner. To the outer end of tube 25 a box 37 is connected which includes spaced apart triangular side pieces 39. Triangular side pieces 39 are moveable together in box 37, which is covered by detector head 21 when it is in its folded-down position. Mirror 19 is then folded into screen frame 18 of image converter 17.

Figure 4:
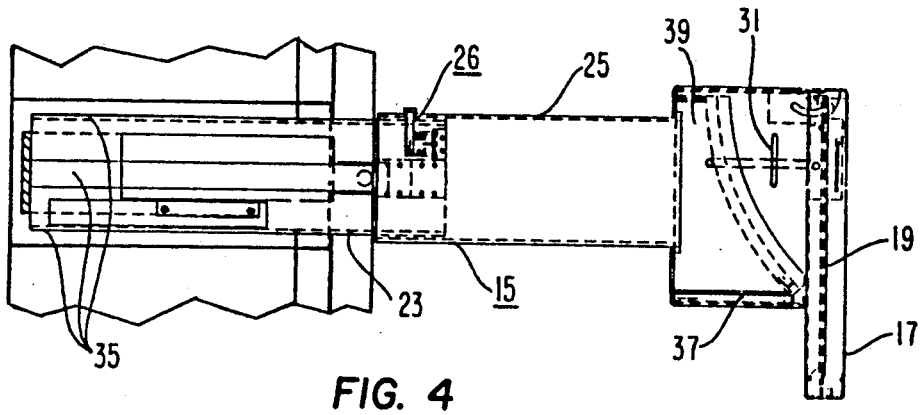

FIG. 4 depicts imaging device 15 in a position in which tube 25 is extracted and in which image converter 17 is still collapsed. Tube 25 is extracted by pulling on handles 31 on both sides of box 37. In its extended position, tube 25 is automatically locked by a spring loaded locking pin mechanism 26, which is shown in more detail in FIGS. 8 and 9.

Figure 5:
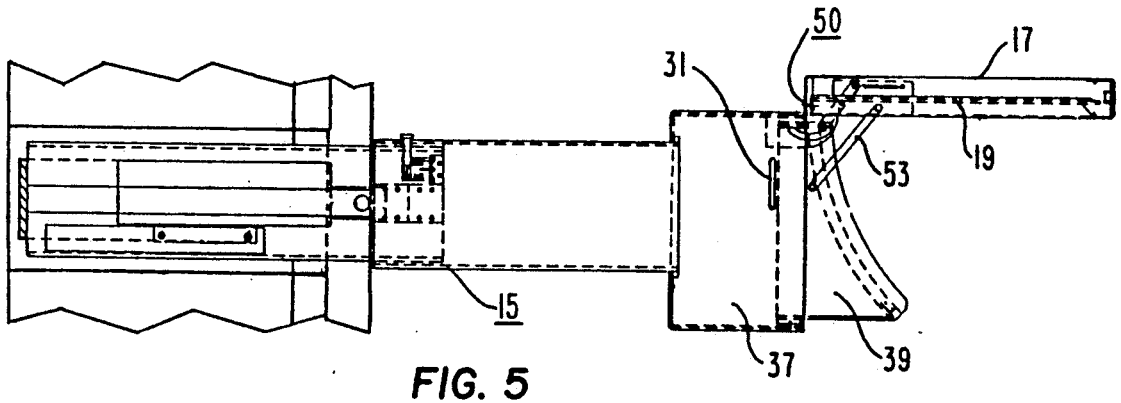

In the position shown in FIG. 5 image converter 17 is lifted up and fixed in place by a spring loaded locking mechanism 50 which is explained in more detail in connection with FIG. 7. When image converter 17 is lifted, triangular side pieces 39 are simultaneously pulled out of box 37 by arms 53 which are coupled to both of image converter 17 and the triangular side pieces 39. Locking mechanism 50 keeps image converter 17 in its horizontal operating position.

Figure 6:
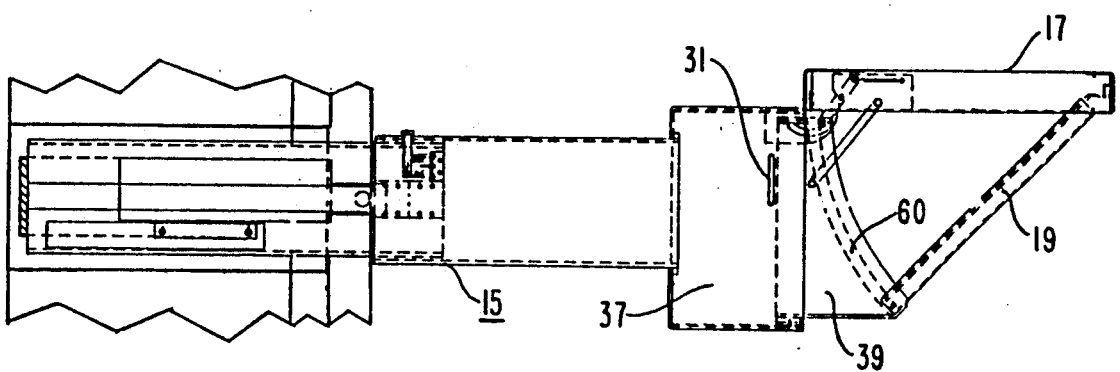

In the position shown in FIG. 6, mirror 19 is in its operating position at an angle of 45 degrees. Mirror 19 is tilted out of screen frame 18 of image converter 17 and thereby guided in tracks 60 formed in triangular side pieces 39. At the same time, flexible side panels (not shown) which are hinged to the underside of said image converter 17 at its distal end, unfold similar to an oriental fan, in order to make the device light-tight between box 37, image converter 17 and mirror 19.

Figure 7:
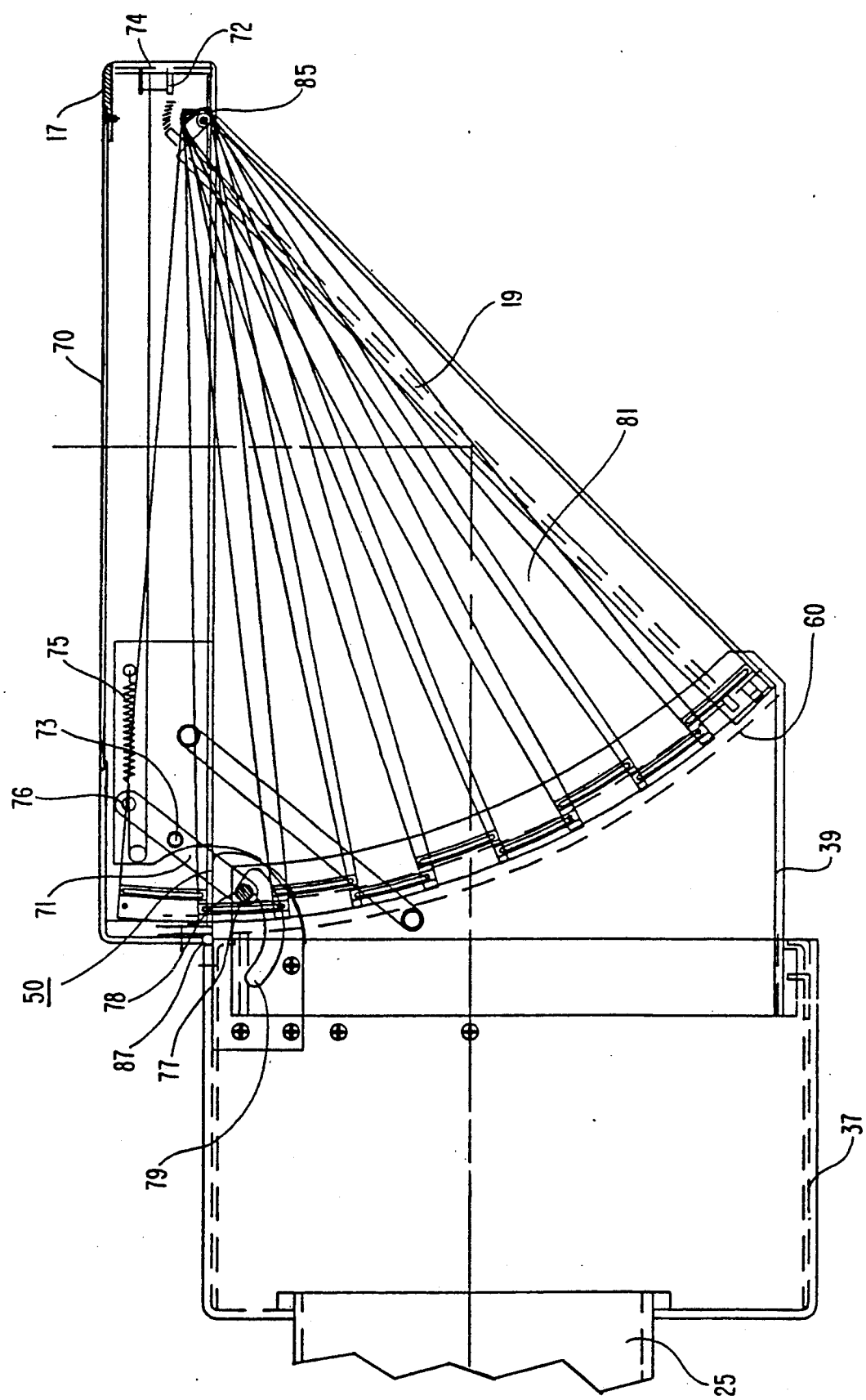
FIG. 7 shows details of a screen head at the front end of the imaging device.

FIG. 7 shows in more detail detector head 21 of imaging device 15 in its operating position. Image converter 17 is lifted when a person grips into a grip dent 72 and lifts screen frame 18 of image converter 17 upwardly from its collapsed position. When image converter 17 is in its horizontal position, screen 70 including the heavy metal foil and the fluorescent foil can be exposed to the radiation beam. Image converter 17 is locked in this horizontal operating position by locking mechanism 50. Locking mechanism 50 comprises a lid lock arm 71 which swivels around pivot 73 under the force of a tension spring 75 coupled to one end of lid lock arm 71 through a pin 76. At the other end of lid lock arm 71 a follower pin 77 is provided which is guided in a guide slot 79. Slot 79 has at its upper end a detent 78 in which guide pin 77 jumps as soon as image converter 17 is in its horizontal operating position. Mirror 19 is then moved to its unfolded position. One end of mirror 19 is coupled to screen frame 18 by a hinge 85 and its other end is moved along tracks 60 of triangular side pieces 39. In its operating position, mirror 19 reflects the images generated by screen 70 through the light channel formed by tubes 23 and 25 and into video camera 33. As previously noted, the side walls of detector head 21 are formed by two light tight panels 81 which fold and unfold similar to an oriental fan.

In order to return image converter 17 into its collapsed position, mirror 19 is moved to its horizontal position around hinge 85. Simultaneously panels 81 are folded into screen frame 18 of image converter 17. Then the operator grips into grip dent 72 which pulls on a cable 83 by moving a cover 74 which partially covers grip dent 72. Cable 83 is connected at its one end to cover 74 and is guided via a pulley 80 to pin 76. When the operator pulls on cable 83 to override tension spring 75, guide pin 77 is moved out of detent 78 and image converter 17 can be collapses around hinge 85. At the same time, triangular side pieces 39 are moved into box 37 by arm 53. After image converter 17 is collapsed to a position similar to that of FIG. 4, tube 25 is slid over tube 23 so that imaging device 15 is back in its storage position.

Figure 8:
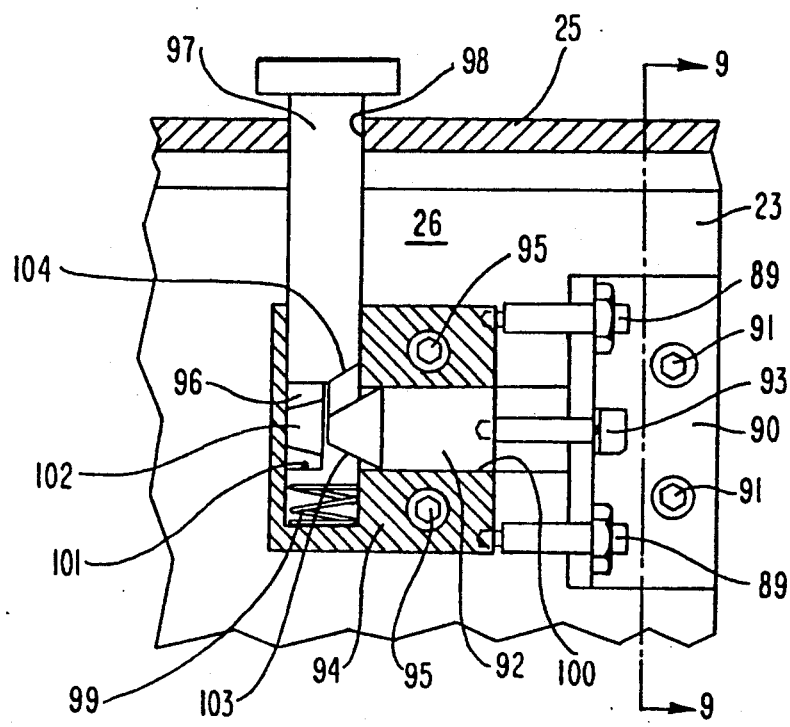
FIG. 8 shows a cross sectional view of a locking mechanism for locking the imaging device in its extended "ready to use" position.

Locking mechanism 26 shown in FIG. 4, as shown in detail in FIG. 8 comprises a bracket 90 which is fastened to the outside of tube 23 at its distal end by screws 91. A lock pin 92 is fastened on bracket 90 by a screw 93. Furthermore, two guide pins 89 are supported by bracket 90. A lock body 94 is connected to the inside of tube 25 by screws 95. Lock body 94 comprises an opening 96 into which a lock release pin 97 extends, which projects also through an opening 98 in tube 25. At its lower end, lock release pin 97 is supported by a pressure spring 99 and held in opening 98 by another spring 101.

When the imaging device is extended and tube 25 is moved along tube 23, as it approaches its fully extended position lock pin 92 projects into opening 100 in lock body 94. At its tip, lock pin 92 has two conical portions 102 and 103. Portion 102 first projects into a corresponding conical opening 104 in lock release pin 97 and causes it to press down against the force of spring 99. When portion 103 reaches opening 104, lock release pin 97 pops up, due to the force of spring 99, and locks both tubes 23 and 25 to prevent further lateral movement.

In order to release locking mechanism 26, a lock release pin 97 is pressed down so that opening 104 releases lock pin 92. Then, together with tube 25, lock release 97 and lock body 94 are moved past stationary lock pin 92.

Figure 9:
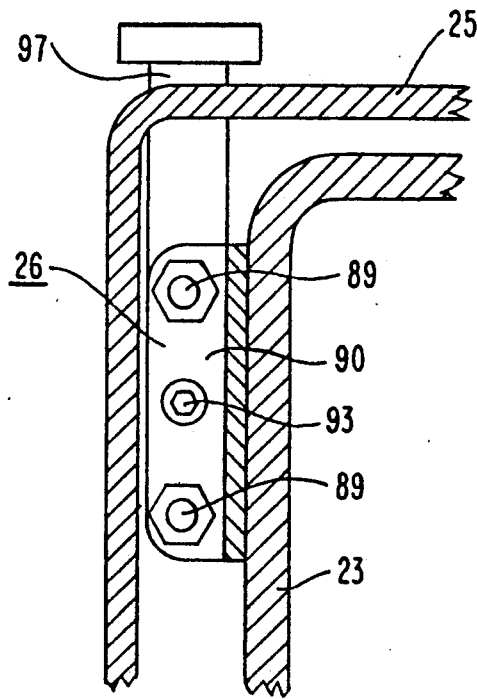
FIG. 9 shows another cross sectional view of the locking mechanism.

FIG. 9 shows a cross sectional view along lines 9—9 of FIG. 8. As can be seen from FIG. 9, locking mechanism 26 is arranged at the side walls of tubes 23 and 25 and between these tubes 23 and 25. In this embodiment, tubes 23 and 25 have a rectangular cross section, but they can also have round cross sections.

There has thus been shown and described a portal imaging device which fulfills all the objects and advantages sought for. Many changes, modifications, variations and other uses and applications of the subject invention will, however, become apparent to those skilled in the art after considering the specification and the accompanying drawings which disclose embodiments thereof. All such changes, modifications, variations and other uses and applications which do not depart from the spirit and scope of the invention are deemed to be covered by the invention which is limited only by the claims which follow.

We claim:

1. A radiation treatment apparatus comprising:
   a stand;
   a gantry supported by said stand;
   a treatment head coupled to said gantry at one end thereof for emitting a radiation beam towards an object;
   an extendable image device coupled to another end of said gantry which is opposite to the treatment head in the trajectory of said radiation beam and at a point past said object, said extendable imaging device including:
   a holding means arranged to be controllably extendable out from inside said gantry and forming a light-tight channel;
   a detector head coupled to the outer end of said holding means, said detector head having:
   an image converting means which in its operating position is essentially perpendicular to said radiation beam and which converts an image represented by said radiation beam into a visible image,
   a reflector coupled with said image converting means for reflecting said visible image into said light-tight channel; and
   a video camera arranged inside said gantry in said light-tight channel for receiving said visible image.

2. A radiation treatment apparatus according to claim 1, wherein said image converting means is arranged in said detector head means in a collapsible manner.

3. A radiation treatment apparatus according to claim 1, wherein said reflector is arranged in said detector head in manner to be foldable towards said image converter.

4. A radiation treatment apparatus according to claim 1, wherein said image converting means comprises a screen frame for holding a metal foil and a fluorescent foil.

5. A radiation treatment apparatus according to claim 1, wherein said reflector comprises a mirror.

6. A radiation treatment apparatus according to claim 1, wherein said holding means is formed of at least two concentrically arranged, different diameter tubes, wherein one tube is connected to said gantry and another tube is connected to said detector head.

7. A radiation treatment apparatus according to claim 1, wherein said holding means is formed of two concentrically arranged different diameter tubes, wherein the tube having the smaller diameter is connected to said gantry and the tube having the bigger diameter is connected to said detector head.

8. A radiation treatment apparatus according to claim 6, wherein said tubes are coupled to each other by slide bearings.

9. A radiation treatment apparatus according to claim 1, wherein said detector head comprises a box which is fastened to said holding means and to which said image converting means is coupled.

10. A radiation treatment apparatus according to claim 9, wherein said image converting means is coupled to said box by a hinge and wherein said reflector is coupled to a distal end of said image converting means in a foldable manner by a further hinge.

11. A radiation treatment apparatus according to claim 10, wherein side walls of said detector head between said image converting means and said reflector are formed by a plurality of lamella coupled to said distal end of said image converting means and being slidably overlapped, said lamella being substantially overlapped in a non-operating position and being barely overlapped in an operating position.

12. A radiation treatment apparatus according to claim 9, wherein said box comprises triangular side pieces which are connected to said converting means by an arm and which are pulled out of the box simultaneously with the movement of said image converting means to its operating position.

13. A radiation treatment apparatus according to claim 12, wherein said image converting means is coupled to said box by a hinge, wherein said reflector is coupled to a distal end of said image converting means in a foldable manner by a further hinge and wherein said triangular side pieces include tracks formed therein for guiding the distal end of said reflector when it is swiveled around said further hinge.

14. A radiation treatment apparatus according to claim 1, wherein said detector head includes a locking means for locking said image converting means in its operating position.

15. A radiation treatment apparatus comprising:
a stand;
a gantry supported by said stand in a rotatable manner;
a treatment head coupled to project out from a front surface of said gantry at one end thereof and emitting a radiation beam towards an object;
an extendable imaging device coupled to another end of said gantry which is opposite to the treatment head in the trajectory of said extendable radiation beam and at a point past said object, said imaging device including:
a holding means arranged to be controllably extendable out from behind said front surface of said gantry and forming a light-tight channel;
a detector head coupled to the outer end of said holding means, said detector head having:
an image converting means collapsibly coupled to said detector head, which in its operating position is essentially perpendicular to said radiation beam and which converts an image represented by said radiation beam into a visible image,
a reflector foldably coupled with said image converting means for reflecting said visible image into said light channel; and
a video camera arranged behind said front surface of said gantry in said light-tight channel for receiving said visible image.

16. A radiation treatment apparatus according to claim 15, wherein said image converting means comprises a screen frame for holding a metal foil and a fluorescent foil.

17. A radiation treatment apparatus according to claim 15, wherein said reflector comprises a mirror.

18. A radiation treatment apparatus according to claim 15, wherein said holding means is formed of at least two concentrically arranged, different diameter tubes, wherein one tube is connected to said gantry and another tube is connected to said detector head.

19. A radiation treatment apparatus according to claim 15, wherein said holding means is formed of two concentrically arranged different diameter tubes, wherein the tube having the smaller diameter is connected to said gantry and the tube having the bigger diameter is connected to said detector head.

20. A radiation treatment apparatus according to claim 18, wherein said tubes are coupled to each other by slide bearings.

21. A radiation treatment apparatus according to claim 15, wherein said detector head comprises a box which is fastened to said holding means and to which said image converting means is coupled.

22. A radiation treatment apparatus according to claim 21, wherein said image converting means is coupled to said box by a hinge and wherein said reflector is coupled to a distal end of said image converting means in a foldable manner by a further hinge.

23. A radiation emitting apparatus comprising:
a stand;
a gantry supported by said stand;
a radiation emitting head coupled to said gantry at one end thereof, for emitting a radiation beam towards an object;
an extendable imaging device coupled to another end of said gantry which is opposite to said head in the trajectory of said radiation beam and at a point past said object, said extendable imaging device including:
a holding means arranged to be controllably extendable from said gantry in a first direction which is perpendicular from said gantry for holding a detector head at the outer end of said holding means, said detector head comprising an image converting means hingedly coupled to said outer end of the extendable holding means so as to be pivotable between an operating and a non-operating position, wherein in its operating position said image converting means is parallel with said first direction so as to intercept said radiation beam and convert an image represented by said radiation beam into a visible image, and in its non-operating position it is pivoted with respect to said outer end of the extendable holding means so as to be perpendicular to said first direction and parallel with said gantry; and
electronic imaging means optically coupled to said converting means for receiving said visible image and generating an electronic signal representative of said visible image.

24. A radiation emitting apparatus according to claim 23, wherein said detector head comprises optical means for directing said visible image to said electronic imaging means.

25. A radiation emitting apparatus according to claim 24, wherein:
said electronic imaging means comprises a video camera; and
said optical means comprises a reflector for reflecting said visible image to said video camera.

26. A radiation emitting apparatus according to claim 25, wherein said reflector comprises a mirror.

* * * * *